United States Patent [19]

Guenther et al.

[11] Patent Number: 5,788,984
[45] Date of Patent: Aug. 4, 1998

[54] GESTODENE-CONTAINING AGENT FOR TRANSDERMAL ADMINISTRATION

[75] Inventors: Clemens Guenther; Ulrich Taeuber; Karin Schmidt-Gollwitzer; Jutta Riedl; Johannes Wilhelm Tack, all of Berlin, Germany

[73] Assignee: Schering Aktiengesellschaft, Berlin, Germany

[21] Appl. No.: 403,137

[22] Filed: Mar. 13, 1995

Related U.S. Application Data

[63] Continuation of Ser. No. 15,974, Feb. 10, 1993, abandoned, which is a continuation of Ser. No. 427,060, Oct. 26, 1989, abandoned.

[30] Foreign Application Priority Data

Oct. 27, 1988 [DE] Germany .......................... 38 36 862.5
Mar. 29, 1989 [DE] Germany .......................... 39 10 578.4

[51] Int. Cl.$^6$ ....................................................... A61F 13/00
[52] U.S. Cl. .......................................... 424/449; 424/448
[58] Field of Search ................................. 424/400, 447, 424/448, 449

[56] References Cited

U.S. PATENT DOCUMENTS

| 4,668,232 | 5/1987 | Cordes et al. | 424/449 |
| 4,780,460 | 10/1988 | Düsterlerg et al. | 514/182 |
| 5,071,657 | 12/1991 | Oloff et al. | |
| 5,422,119 | 6/1995 | Casper | 424/449 |
| 5,580,572 | 12/1996 | Mikler et al. | 424/448 |
| 5,605,702 | 2/1997 | Teillaud et al. | 424/448 |

FOREIGN PATENT DOCUMENTS 2208147  3/1989  United Kingdom.

*Primary Examiner*—S. Mark Clardy
*Assistant Examiner*—Robert H. Harrison
*Attorney, Agent, or Firm*—Millen, White, Zelano, & Branigan, P.C.

[57] ABSTRACT

An agent for transdermal administration contains gestodene, optionally in combination with one or more estrogen(s).

38 Claims, No Drawings

GESTODENE-CONTAINING AGENT FOR TRANSDERMAL ADMINISTRATION

This application is a continuation of application Ser. No. 08/015,974, filed Feb. 10, 1993, now abandoned, which is a continuation of Ser. No. 07/427,060, filed Oct. 26, 1989, now abandoned.

SUMMARY OF THE INVENTION

The invention relates to an agent for transdermal administration, characterized in that it contains gestodene, optionally in combination with one or several estrogen.(s).

Gestodene (13-ethyl-17β-hydroxy-18,19-dinor-17α-pregna-4,15-dien-3-one), a compound of the formula

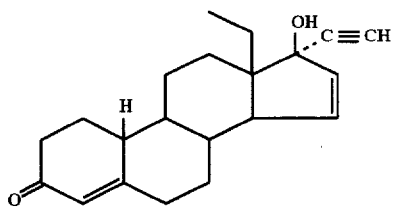

is, as is known, a pharmacologically active substance having extraordinarily strong gestagen activity and being used, in combination with estrogen-active compounds, for the production of contraceptives to be administered orally ("Femovan").

It has now been found that gestodene, optionally in combination with one or several estrogen(s), can be utilized with great success for the production of an agent for the transdermal administration of the active compound or compound mixture.

Medicinal agents that are to be administered transdermally have the advantage, as is known, that they permit more uniform delivery of the active compound over a longer period of time than normally possible with agents that must be differently administered—for example orally. These properties can be beneficially exploited in a number of endocrine disorders. However, for steroid hormones of poor water solubility, such as, for example, the gestagens, it is usually rather problematic to produce transdermal systems ensuring penetration of the active agent through the skin to an extent adequate for therapy.

It has now been found that it is surprisingly possible with the aid of the agent of this invention to achieve a therapeutically sufficient, very uniform penetration rate of the steroid hormones through the skin whereas this effect can only be conditionally attained with the known agents which contain steroid hormones and are to be administered transdermally. (EP-A 137278 and EP-A 275716.)

The abstract of EP 0 137 278 states a means for transdermal application of drugs is claimed which is characterized in that the drug is at least 50% dissolved in a non-flowable, physiologically harmless gel which is microdispersed in a cross-linked silicone elastomer.

Suitable estrogens for the agent according to this invention are, for example, estradiol, estriol, ethynyl-estradiol, and their esters (EP-A 163596), such as estradiol dipropionate, estradiol dihexanoate, and estradiol didecanoate. The combination preparations of this invention can contain, besides gestodene, preferably 1 to 3—especially 1 to 2 estrogen(s).

For preparing pharmaceutical products, the active agent or the active agent mixture can be dissolved or suspended in suitable volatile solvents and/or penetration-enhancing media. The resultant solutions or suspensions can be combined with the usual auxiliary agents, such as matrix-forming media and bactericides, and can be dispensed, if desired, after sterilization into customary dosing containers. However, on the other hand, it is likewise possible to further process these solutions or suspensions with the inclusion of emulsifiers and water into lotions or ointments. It is also possible to produce sprays—if desired with the addition of a propellant gas—and these can be filled into the customary metering containers.

Suitable volatile solvents include, for example, lower alcohols, ketones or lower carboxylic acid esters, such as ethanol, isopropanol, acetone, or ethyl acetate, polar ethers, such as tetrahydrofuran, lower hydrocarbons, such as cyclohexane or naphtha, or also halogenated hydrocarbons, such as dichloromethane, trichloromethane, trichlorotrifluoroethane, and trichlorofluoromethane. Mixtures of these solvents are likewise suitable.

Penetration-enhancing agents that can be used are, for example, alcohols, such as 1,2-propanediol or benzyl alcohol, saturated and unsaturated fatty alcohols with 8–18 carbon atoms, such as lauryl alcohol or cetyl alcohol, hydrocarbons, such as mineral oil, saturated and unsaturated fatty acids of 8–18 carbon atoms, such as stearic acid or oleic acid, fatty acid esters of the general formula $$CH_3-(CH_2)_n-COOR$$

wherein
  n is a number from 8 to 18 and
  R is an alkyl residue of maximally 6 carbon atoms, or dicarboxylic acid diesters of the general formula $$R'OCO(CH_2)_mCOOR'$$

wherein
  m is a number from 4 to 8 and
  R' in each case means an alkyl residue of maximally 6 carbon atoms Fatty acid esters suitable for the agent of this invention are, for example, those of lauric acid, myristic acid, stearic acid and palmitic acid, e.g., the methyl esters, ethyl esters, propyl esters, isopropyl esters, butyl esters, sec-butyl esters, isobutyl esters of these acids. Especially preferred esters are those of myristic acid, such as its methyl ester and particularly its isopropyl ester. Suitable dicarboxylic acid diesters are, for example, the diisopropyl adipate, diisobutyl adipate and diisopropyl sebacate. Also, mixtures of these penetration-enhancing media are suitable for the preparation of the agent of this invention.

The concentration in which the active agent or active agent mixture is optimally dissolved or suspended in the solvent amounts, for gestodene, usually to 0.01–25% by weight. In case of the estrogens, the concentration is naturally dependent on the type of active compound employed and on the desired individual dose; in the particular instance, this concentration must be determined by means of the routine preliminary tests which are familiar to a person skilled in the art, e.g., the determination of the attainable blood plasma concentrations of active compound, in connection with selected agents of this invention. See, e.g., "Weiner klinische Wochenschrift" 93, 1981, 601–604, or U.S. Pat. No. 4,719,054. In general, active agent concentrations of 0.01–25% by weight of estrogen in the agent of this invention will be adequate also in this case. The weight ratio of gestodene to the estrogen(s) is, in the combination preparations, 5:1 to 1:10, generally.

The determination of the extent of the rate of percutaneous absorption by the agents of this invention can take place, for example, by means of radioactively labeled steroid hormones.

Freshly prepared skin from the abdomen of hairless mice, freed of subcutaneous fat, is clamped into a Franz diffusion cell containing,as the trapping liquid, isotonic polyethylene glycol (MW 400) solution or phosphate buffer solution, pH 7. Then 2 μl of test solution is applied to the skin and the content of steroid hormone that has entered the trapping liquid is determined after 24, 48 and 72 hours by means of liquid scintillation counting.

The test involved a 2% by weight solution of gestodene in isopropyl myristate (Test A) and paraffin (Test B).

Table 1 below demonstrates the results obtained in this test:

TABLE 1

Percutaneous Flow in ng Gestodene per cm$^2$ of Skin Surface and Hour

| Time Interval | Test A Percutaneous Flow | Test B Percutaneous Flow |
| --- | --- | --- |
| 00–24 h | 546 | 755 |
| 24–48 h | 379 | 245 |
| 48–72 h | 287 | 100 |

It can furthermore be shown that gestodene exhibits adequate percutaneous absorption in its not radioactively labeled form, dissolved in 1,2-propane-diol (Test C) or in isopropyl myristate (Test D) in case of postmenopausal women.

The test involved 0.4 mg of gestodene, dissolved in respectively 200 μl of the corresponding vehicle, applied for 48 hours to a skin area of 10 cm$^2$.

Table 2 below demonstrates the results obtained in this test:

TABLE 2

Percutaneous Flow in ng Gestodene per cm$^2$ of Skin Surface and Hour

| | Steady State Plasma Level pg/ml | Percutaneous Flow ng/cm$^2$/h at 24–48 h |
| --- | --- | --- |
| Test C | 250 | 43 |
| Test D | 337 | 57 |

An even more uniform administration with a set dosage of the active agent or active agent mixture can be obtained by embedding the active agent or the mixture in a transdermal therapeutic system (TTS). Suitable transdermal therapeutic systems are those usually employed for the percutaneous administration of active agents [Yie W. Chien: "Transdermal Controlled Systemic Medications", Marcel Dekker, Inc., New York and Basel, 1987; Dr. Richard Baker: "Analysis of Transdermal Drug Delivery Patents 1934 to 1984" and "Analysis of Recent Transdermal Delivery Patents, 1984–1986 and Enhancers", Membrane Technology and Research, 1030 Hamilton Court, Menlo Park, Calif. 94025 (415) 328-2228].

Thus, it is possible, for example, to utilize such a transdermal therapeutic system which consists of (a) an impermeable cover layer,
a medicine layer adhering to the cover layer, containing the gestodene, optionally the estrogen(s) and, if desired, penetration-enhancing media and being permeable for these components, this medicine layer being pressure-sensitive or being covered or surrounded by a skin adhesive, wherein this skin adhesive can likewise contain penetration-enhancing media, and a protective layer that can be pulled off, or (b) an impermeable cover layer,
a medicine reservoir located on or in the cover layer and containing the gestodene, optionally the estrogen (s) and, if desired, penetration-enhancing media,
a polymer layer permeable for these components,
a layer of skin adhesive which is permeable and optionally contains penetration-enhancing media, and
a protective layer that can be pulled off.

A transdermal therapeutic system according to version (a) represents a simple matrix system. It can be produced, for example, as follows:

A solution or suspension of 1–25% by weight of active agent or active agent mixture, 0–40% by weight of a penetration-enhancing medium, 30–70% by weight of a medically customary adhesive, filled up to 100% by weight with a suitable volatile solvent, is spread onto a flat impermeable cover layer and, after drying, provided with a removable protective layer.

When using a medically customary matrix-forming agent which, after drying of the system, does not adhere, or does not adhere adequately, to the skin, then the system can be additionally covered or surrounded with a skin adhesive prior to application of the removable protective layer.

Suitable solvents and penetration-enhancing media are, for example, the aforementioned liquids of this type. Suitable as the medically customary adhesives are, for example, polyacrylates, silicones, polyurethanes, as well as natural or synthetic elastomers. Further matrix-forming agents that are suitable are cellulose ethers, polyvinyl compounds, or silicates.

Suitable as the protective layers are all films usually employed in case of transdermal therapeutic systems. Such films are, for example, siliconized or coated with a fluoropolymer.

The cover layer in this system can be, for example, films of polyethylene or polyester having a thickness of 10–100 μm and being selectively pigmented or metallized. The medicine layer applied thereto preferably has a thickness of 20–500 μm. The delivery of the active agents takes place preferably over an area of 5–100 cm$^2$.

A transdermal therapeutic system according to version (b) can be produced, for example, as follows:

An impermeable film is deformed by heat and/or tensile stress so that a bulge is produced having a volume of 0.1–3 ml. This bulge is filled with an active-agent-containing solution or suspension with 1–50% by weight of active agent or active agent mixture in a penetration-enhancing medium. The solution or suspension containing the active ingredient can also be thickened with up to 10% by weight of a matrix-forming agent.

The cover of the reservoir toward the skin is constituted by a permeable polymer layer that has been heat-sealed or glued in place, a permeable skin adhesive layer and a removable protective layer being applied on top of this cover.

The above-mentioned penetration-enhancing media can be utilized in this system. An example of a permeable polymer layer is a 20–200 μm thick film of cellulose esters, cellulose ethers, silicones, or polyolefin compounds. By variation of this polymer layer, the diffusion rate of the active agent or active agent mixture can be varied within wide limits using well known principles perhaps with a few routine preliminary experiments, e.g., as discussed in the literature referenced above.

Suitable as the adhesive and the protective layer are the same materials described in the transdermal therapeutic system according to version (a).

Thus, by a simple variation of the different parameters, transdermal therapeutic systems with differing delivery rates of active agent or active agent mixture can be produced; these can be packaged, for example, into aluminum foil for the purpose of storage.

It has been mentioned above that the agent of this invention for transdermal administration can also be prepared as a lotion, an ointment, or as a spray. Such preparations are advantageous in those cases where no occlusion is desirable.

An emulsion gel for transdermal administration comprises, for example, the active agent or active agent mixture, penetration-enhancing media, emulsifiers (ambiphilic representatives of the penetration-enhancing media being able to serve as emulsifiers), and optionally matrix-forming agents. A typical formulation comprises 0.1-25% by weight of active ingredient or active ingredient mixture, 0-10% by weight of emulsifier, 0-5% by weight of matrix-forming material, 0-50% by weight of penetration-enhancing media, and water up to 100% by weight. The agent is emulsified in the usual way and combined, if required, with the customary antioxidants, preservatives, etc.

Monophase gels are obtained, for example, by dissolving or suspending the active compound or the active compound mixture in solvents such as water, lower alcohols, or mixtures thereof, optionally with the addition of penetration-enhancing media and thickening with matrix-forming materials.

Typical formulations for such gels contain 0.01-25% by weight of active compound or active compound mixture, 1-20% by weight of matrix-forming material, 0-40% by weight of penetration-enhancing media, supplemented with the solvent to give 100% by weight.

These gels can likewise contain antioxidants, preservatives, etc., if desired.

A typical spray formulation is, for example, the following:

1-25% by weight of active compound or active compound mixture, 0-20% by weight of matrix-forming material, 0-60% by weight of penetration-enhancing media, supplemented to give 100% by weight with solvents and optionally propellant media. In case compressed-gas packages are utilized, the propellant medium can be omitted.

The gestodene-containing agents of this invention for transdermal administration can be utilized for the treatment of the same diseases as the previously known agents containing highly effective gestagens and to be administered orally, for example. Moreover, the preparations of this invention which optionally contain estrogen can also be used for contraception. The agents of this invention exhibit special advantages in the treatment of diseases requiring long-term treatment with a relatively high dosage of the active compounds, e.g., from many months to many years. In this case, administration frequency can be substantially reduced, and an essentially uniform blood plasma level can be achieved. It is furthermore advantageous that gastrointestinal side effects are not to be expected and, in case of estrogen-containing combination preparations, the first liver passage is circumvented, and that the dose of estrogen can be reduced.

These advantages make the estrogen-free monotherapeutic agents of the present invention especially suitable for the treatment of, for example, endometriosis, gestagen-dependent tumors, benign breast diseases, or premenstrual syndrome.

Transdermal utilization of estrogens in a sequential or continuous combination with gestodene offers special advantages, for example, for the treatment of climacteric disorders, for prevention of osteoporosis, for cycle regulation, and for cycle stabilization.

The transdermal agents of this invention can be administered analogously to the administration of other transdermal compositions. Thus, when gestodene is administered alone, typically, the administration will be made through the skin located at various parts of the body but preferably at the hips, the ventral and lateral parts of the thorax, the thighs and the ventral side of the arms. When gestodene is coadministered with an estrogen or in conjunction with a separate administration of an estrogen, the transdermal application is typically made through skin located at various parts of the body but preferably at the hips, the ventral and lateral parts of the thorax, the thighs and the ventral side of the arms. Suitable locations for administration are essentially the same irrespective of the form of the transdermal composition, e.g., the usual transdermal patches or an ointment, lotion or spray, for example. Suitable times of application can be determined routinely for a given disease or state and will typically be fully analogous to conventional administrations of gestodene and/or estrogens.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire texts of all applications, patents and publications, if any, cited above and below, and of corresponding applications German P 38 36 862.5, filed Oct. 27, 1988 and German P 39 10 587.4, filed Mar. 29, 1989, are hereby incorporated by reference.

The following commercially available products were used in these examples:

Polyester film, thickness 0.074 mm ("SkotchPak" 1009), manufacturer: 3M; polypropylene film ("Celgard" 2500), manufacturer: Celanese; liner film "SkotchPak" 1022 and 1360, manufacturer: 3M; transfer adhesive 9871, manufacturer: 3M; polyacrylic ester adhesive, type "Sichello" J6610-21, manufacturer: Henkel KG; silicone adhesive, type X-7-2960, manufacturer: Dow Corning; and hydroxypropylcellulose, type "Klucel" HXF, manufacturer: Hercules.

EXAMPLE 1

Under agitation, and in succession, 0.8 g of gestodene and 8.0 g of 1,2-propanediol are dissolved or suspended in 62.4 g of a 50% solution of silicone adhesive in naphtha (since the adhesives are turbid, no clear decision can be rendered on whether a complete solution has taken place). After degasifying the batch, the solution/suspension is applied to polyester sheet by means of a coating device in such a way that, after removal of the volatile solvent, a uniform film of 40 g/m$^2$ of solid matter applied is obtained. Subsequently, the polyester sheet is laminated to a fluoropolymer-coated polyester liner. The resultant laminate is divided by means of a punching device into individual plasters having an area of 10 cm$^2$ and packaged into aluminum foil. The plaster adheres to the skin after the liner film has been pulled off.

The determination of the content yields a uniform active compound distribution of 0.08 mg/cm$^2$ in the agent. The plaster is furthermore characterized by way of its in vitro delivery behavior in water over 30 hours at 32° C. From a typical matrix release curve, after linearization, a delivery rate for gestodene is calculated of 0.4 µg/cm$^2$/h.

EXAMPLE 2

Under agitation, and in succession, 5.0 g of gestodene and 10.0 g of isopropyl myristate are dissolved or suspended in 170 g of a 50% solution of polyacrylate adhesive in acetone/naphtha. After the batch has been degasified, the solution/suspension is applied to polyester sheeting by means of a coating device in such a way that, after removal of the volatile solvents, a uniform film is produced of 100 g/m$^2$ of solid matter application. Subsequently, the sheeting is laminated with a siliconized liner film free of active agent. The resultant laminate is divided by means of a punching device into individual plasters having an area of 10 cm$^2$ and packaged into aluminum foil. The plaster adheres to the skin after the liner film has been pulled off.

The gestodene content in the agent is 0.5 mg/cm$^2$. The average delivery rate of gestodene is 0.3 µg/cm$^2$/h.

EXAMPLE 3

Under agitation, and in succession, 3.5 g of estradiol 3.5 g of gestodene and 7.0 g of 1,2-propanediol with 10% 1-dodecanol are dissolved or suspended in 112 g of a 50% solution of polyacrylate adhesive in acetone/naphtha. After the batch has been degasified, the solution/suspension is applied to polyester sheeting by means of a coating device in such a way that, after removal of the volatile solvents, a uniform film is produced of 70 g/m$^2$ solid applied matter. Then the sheeting is laminated with a siliconized liner film free of active ingredient. The thus-obtained laminate is divided by means of a punching device into individual plasters of 10 cm$^2$ area and packaged into aluminum foil. The plaster adheres to the skin after the liner film has been pulled off.

The estradiol content and the gestodene content are the same, with 0.35 mg/cm$^2$.

This plaster yields, within 48 hours in an in vitro test in water of 320° C., with 0.6 µg/cm$^2$/h, higher delivery rates for estradiol than for gestodene, the value for the latter being 0.4 µg/cm$^2$/h.

EXAMPLE 4

A polyester sheet having a diameter of 7.4 cm is shaped by means of tension and heat in such a way that a round bulge is produced having an area of 10 cm$^2$. This bulge is filled with 1 ml of a suspension of 2.5 mg of estradiol and 2.5 mg of gestodene in 1,2-propanediol containing 10% lauric acid. A polypropylene or cellulose acetate butyrate sheet is heat-sealed thereon along the rim. Depending on the pressure per unit time, the sealing temperature ranges between 70° C. and 100° C. Pressure-sensitive adhesive film is transferred to the permeable polymer layer. The plaster is provided with a liner and packaged into aluminum foil.

This plaster yields, for both active agents, identical in vitro delivery rates in water of 320° C. of between 0.02 and 0.08 µg/cm$^2$/h.

EXAMPLE 5

In succession, 0.2 g of estradiol 0.02 g of gestodene 10.0 g of 1,2-propanediol and 10.0 g of isopropyl myristate are dissolved in 76.78 g of ethanol (96% by volume) or isopropanol. Then the solution is combined with 3 g of hydroxypropylcellulose and the air is removed from the solution. After 2 hours of steeping time, the gel is filled into aluminum tubes having a triple internal protection varnish coating.

The determination of the content shows homogeneous active agent distribution in the gel with values of 95% with 105% of the desired value.

EXAMPLE 6

20.00 g of gestodene is dissolved in 1000 g of isopropyl myristate, filtered under sterile conditions, and dispensed under aseptic conditions into medicine bottles of 5 ml each.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A pharmaceutical composition for transdermal administration comprising:
   gestodene and a pharmaceutically acceptable carrier for transdermal administration, and, optionally, an estrogenic compound,
   wherein the amount of gestodene dissolved or suspended in said pharmaceutically acceptable carrier is 0.01–25 wt. % and the amount of said estrogenic compound, if present dissolved or suspended in said pharmaceutically acceptable carrier is 0.01–25 wt. %.

2. A composition of claim 1, which is an ointment, lotion or spray.

3. A composition of claim 1, comprising no estrogenic compound.

4. A composition of claim 1 comprising an estrogenic compound.

5. A composition of claim 4, wherein the estrogen is estradiol, estriol, 17-ethynylestradiol, or an ester of these compounds.

6. A composition of claim 4, comprising 1 or 2 estrogenic compounds.

7. A composition according to claim 4, wherein the weight ratio of gestodene to estrogenic compound is 5:1–1:10.

8. A composition according to claim 1, wherein said pharmaceutically acceptable carrier comprises at least one penetration-enhancing agent wherein said agent is
   1,2-propanediol,
   benzyl alcohol,
   a saturated or unsaturated fatty alcohol having 8–18 C atoms,
   mineral oil,
   a saturated or unsaturated fatty acid of 8–18 C atoms,
   a fatty acid ester of the formula $C_3$—$(CH_2)_n$—COOR wherein n is 8–18 and R is alkyl having up to 6 C atoms, a dicarboxylic acid diester of the formula R'OCO(CH$_2$)$_m$COOR' wherein m is 4–8 and R' is, in each case independently, alkyl of up to 6 C atoms, or combinations thereof.

9. An article for transdermal administration comprising:

a pharmaceutical composition comprising gestodene and a pharmaceutically acceptable carrier for transdermal administration, and, optionally, an estrogenic compound;

wherein the amount of gestodene dissolved or suspended in said pharmaceutically acceptable carrier is 0.01–25 wt. % and the amount of said estrogenic compound, if present, dissolved or suspended in said pharmaceutically acceptable carrier is 0.01–25 wt. %; and a transdermal therapeutic system wherein said composition is in said transdermal therapeutic system.

10. An article according to claim 9, comprising an estrogenic compound.

11. An article of claim 10 wherein said composition contains an estrogenic compound which is estradiol, an ester of estradiol, estriol, an ester of estriol, 17-ethynylestradiol or an ester of 17-ethynylestradiol.

12. An article of claim 9, wherein the transdermal therapeutic system comprises:

(a) an impermeable cover layer, a medicinal layer adhering to the cover layer and permeable to these components, and containing the gestodene and optionally an estrogen, and, optionally, penetration-enhancing media, this medicinal layer being pressure-sensitive, skin adhesive or being covered or surrounded by a skin adhesive, wherein this skin adhesive optionally contains penetration-enhancing media, and a protective layer that can be pulled off, or (b) an impermeable cover layer, a medicinal reservoir located on or in the cover layer and containing gestodene, optionally an estrogen and, optionally, penetration-enhancing media, a polymer layer permeable to these components, a layer of skin adhesive which is permeable and optionally contains penetration-enhancing media, and a protective layer that can be pulled off.

13. An article according to claim 9, comprising no estrogenic compound.

14. An article according to claim 10, comprising 1–2 estrogenic compounds.

15. An article according to claim 10, wherein the weight ratio of gestodene to estrogenic compound is 5:1–1:10.

16. An article according to claim 9, wherein said pharmaceutically acceptable carrier comprises at least one penetration-enhancing agent wherein said agent is 1,2-propanediol, benzyl alcohol, a saturated or unsaturated fatty alcohol having 8–18 C atoms, mineral oil, a saturated or unsaturated fatty acid of 8–18 C atoms, a fatty acid ester of the formula C$_3$—(CH$_2$)$_n$—COOR wherein n is 8–18 and R is alkyl having up to 6 C atoms, a dicarboxylic acid diester of the formula R'OCO(CH$_2$)$_m$COOR' wherein m is 4–8 and R' is, in each case independently, alkyl of up to 6 C atoms, or combinations thereof.

17. An article according to claim 9, wherein the amount of gestogen is 0.8–5 mg.

18. In a method of administering gestodene to a patient, the improvement comprising administering gestodene transdermally, optionally in combination with an estrogenic compound, wherein said gestodene and optional estrogenic compound are dissolved or suspended in a pharmaceutically acceptable carrier, and wherein the amount of gestodene dissolved or suspended in said pharmaceutically acceptable carrier is 0.01–25 wt. % and the amount of said estrogenic compound, if present, dissolved or suspended in said pharmaceutically acceptable carrier is 0.01–25 wt. %.

19. A method of claim 18, wherein gestodene is administered in the form of an ointment, lotion or spray.

20. A method of claim 18, wherein no estrogenic compound is administered.

21. A method of claim 18, wherein an estrogenic compound is administered.

22. A method of claim 21, wherein 1 or 2 estrogenic compounds are administered.

23. A method of claim 21, wherein the estrogen is estradiol, estriol, 17-ethynylestradiol, or an ester of these compounds.

24. A method of claim 18 for treating endometriosis, a gestagen-dependent tumor, or premenstrual syndrome.

25. A method of claim 18 for treating climacteric symptoms, for prevention of osteoporosis, for cycle regulation or for cycle stabilization.

26. A method of claim 25 comprising also administering an estrogenic compound.

27. A method according to claim 21, wherein the weight ratio of gestodene to estrogenic compound is 5:1–1:10.

28. A method according to claim 18, wherein said pharmaceutically acceptable carrier comprises at least one penetration-enhancing agent wherein said agent is 1,2-propanediol, benzyl alcohol, a saturated or unsaturated fatty alcohol having 8–18 C atoms, mineral oil, a saturated or unsaturated fatty acid of 8–18 C atoms, a fatty acid ester of the formula C$_3$—(CH$_2$)$_n$—COOR wherein n is 8–18 and R is alkyl having up to 6 C atoms, a dicarboxylic acid diester of the formula R'OCO(CH$_2$)$_m$COOR' wherein m is 4–8 and R' is, in each case independently, alkyl of up to 6 C atoms, or combinations thereof.

29. A method according to claim 18, wherein the amount of gestogen is 0.8–5 mg.

30. In a method of administering gestodene to a patient, the improvement comprising administering gestodene, optionally in combination with an estrogenic compound, by a transdermal therapeutic system, wherein said gestodene and optional estrogenic compound are dissolved or suspended in a pharmaceutically acceptable carrier, and wherein the amount of gestodene dissolved or suspended in said pharmaceutically acceptable carrier is 0.01–25 wt. % and the amount of said estrogenic compound, if present, dissolved or suspended in said pharmaceutically acceptable carrier is 0.01–25 wt. %.

31. A method of claim 30, wherein said estrogenic compound is estradiol, an ester of estradiol, estriol, an ester of estriol, 17-ethynylestradiol or an ester of 17-ethynylestradiol.

32. A method of claim 30, wherein the transdermal therapeutic system comprises:

(a) an impermeable cover layer, a medicinal layer adhering to the cover layer and permeable to these components, and containing the gestodene and optionally an estrogen, and, optionally, penetration-enhancing media, this medicinal layer being pressure-sensitive, skin adhesive or being covered or surrounded by a skin adhesive, wherein this skin adhesive optionally contains penetration-enhancing media, and a protective layer that can be pulled off, or (b) an impermeable cover layer, a medicinal reservoir located on or in the cover layer and containing gestodene, optionally an estrogen and, optionally, penetration-enhancing media, a polymer layer permeable to these components, a layer of skin adhesive which is permeable and optionally contains penetration-enhancing media, and a protective layer that can be pulled off.

33. A method according to claim 30, wherein no estrogenic compound is administered.

34. A method according to claim 30, wherein an estrogenic compound is administered.

35. A method according to claim 34, wherein the weight ratio of gestodene to estrogenic compound is 5:1–1:10.

36. A method according to claim 30, wherein said pharmaceutically acceptable carrier comprises at least one penetration-enhancing agent wherein said agent is 1,2-propanediol, benzyl alcohol, a saturated or unsaturated fatty alcohol having 8–18 C atoms, mineral oil, a saturated or unsaturated fatty acid of 8–18 C atoms, a fatty acid ester of the formula $C_3$—$(CH_2)_n$—COOR wherein n is 8–18 and R is alkyl having up to 6 C atoms, a dicarboxylic acid diester of the formula R'OCO$(CH_2)_m$COOR' wherein m is 4–8 and R' is, in each case independently, alkyl of up to 6 C atoms, or combinations thereof.

37. A method according to claim 30, wherein the amount of gestogen is 0.8–5 mg.

38. A method according to claim 30, wherein the delivery rate of gestodene is 0.02–0.04 µg/cm²/h.

* * * * *